United States Patent [19]

Dickson

[11] Patent Number: 4,519,251

[45] Date of Patent: May 28, 1985

[54] ROLLER-TYPE ULTRASONIC INSPECTION DEVICE WITH ACOUSTICAL ISOLATION

[75] Inventor: John K. Dickson, Waddesdon, England

[73] Assignee: Schlumberger Electronics (UK) Limited, Farnborough, England

[21] Appl. No.: 529,812

[22] Filed: Sep. 6, 1983

[30] Foreign Application Priority Data

Sep. 15, 1982 [GB] United Kingdom ............... 8226283

[51] Int. Cl.³ .............................................. G01N 29/00
[52] U.S. Cl. ........................................ 73/639; 73/644
[58] Field of Search ................ 73/635, 639, 624, 644

[56] References Cited

U.S. PATENT DOCUMENTS

| | | | |
|---|---|---|---|
| 3,546,924 | 12/1970 | Nussbaum et al. | 73/644 |
| 3,573,515 | 4/1971 | Stombaugh | 73/639 |
| 4,088,028 | 5/1978 | Hildebrandt | 73/624 |
| 4,202,216 | 5/1980 | Bull et al. | 73/639 |
| 4,208,915 | 6/1980 | Edwards | 73/639 |
| 4,217,782 | 8/1980 | Pont | 73/639 |
| 4,302,976 | 12/1981 | Bull | 73/639 |

FOREIGN PATENT DOCUMENTS

| | | |
|---|---|---|
| 1197695 | 7/1970 | Great Britain. |
| 1294404 | 10/1972 | United Kingdom ............... 73/639 |
| 1347356 | 2/1974 | Great Britain. |
| 1373881 | 11/1974 | Great Britain. |
| 8000749 | 4/1980 | PCT. |
| 2043248 | 10/1980 | Great Britain. |

*Primary Examiner*—Howard A. Birmiel
*Attorney, Agent, or Firm*—Dale Gaudier

[57] ABSTRACT

A roller-type ultrasonic probe comprises a support having two parallel limbs, and two coaxially aligned hubs each extending from a respective limb towards the other. An ultrasonic transmitter is mounted in one hub, a receiver is mounted in the other, and an acoustic screen is disposed between the adjacent ends of the hubs. Respective glycerine-filled rollers are mounted on each hub, and a common (or split) tire fits over both rollers. The respective axes of the transmitter and the receiver are preferably inclined at about 5° and 7° respectively towards the radially extending plane between the transmitter and receiver. The arrangement is particularly compact, and facilitates high-resolution ultrasonic investigation of bond quality in glass or carbon-fibre reinforced plastic sheets and other laminates.

9 Claims, 1 Drawing Figure

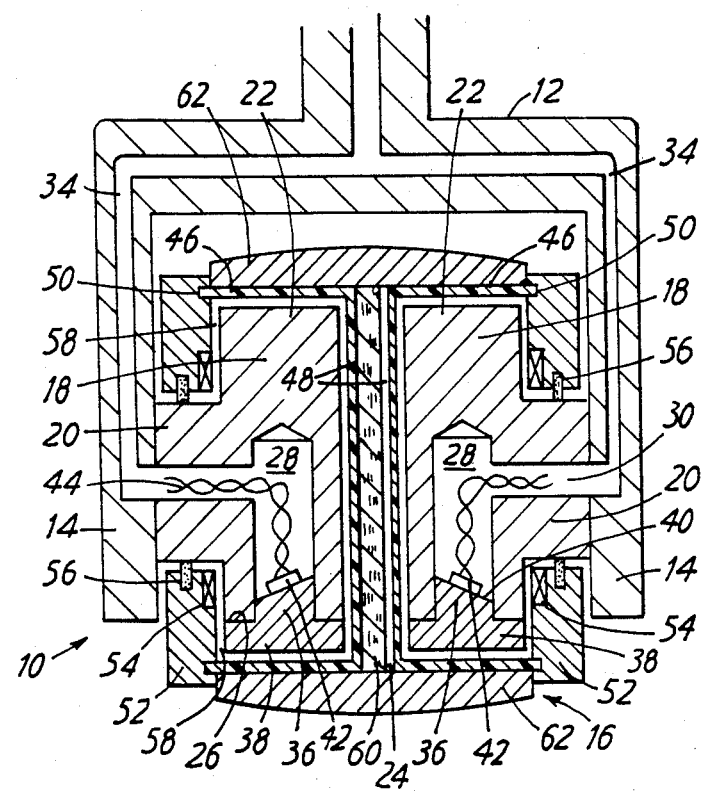

ROLLER-TYPE ULTRASONIC INSPECTION DEVICE WITH ACOUSTICAL ISOLATION

This invention relates to ultrasonic inspection devices, and is more particularly concerned with roller-type ultrasonic inspection devices.

It is known to inspect moving sheet-like objects for defects using ultrasonic inspection apparatus comprising two roller-type ultrasonic inspection devices, which are spaced apart along a line transverse to the direction of movement of the object and urged into rolling contact with the object. One of the devices is operated as an ultrasonic transmitter, while the other is operated as an ultrasonic receiver, and the apparatus is therefore able to detect defects in the longitudinal region, or strip, of the object between the two devices.

However, this apparatus suffers from the drawback that the use of two spaced roller-type inspection devices imposes a limit on the resolution of the apparatus, ie a limit on the minimum size of defect which can be reliably detected, this limit being at least partly due to the minimum spacing between the two inspection devices which can be physically achieved in practice. It is therefore an object of the present invention to provide a roller-type ultrasonic inspection device which alleviates this drawback.

According to the present invention, there is provided a roller-type ultrasonic inspection device for use in the ultrasonic inspection of an object, the device comprising:

a support having two spaced-apart generally parallel limbs;

two substantially coaxially aligned hub members each projecting from a respective one of the limbs towards the other hub member, the adjacent ends of the hub members defining a gap therebetween;

an acoustic screening member disposed in said gap;

a respective ultrasonic transducer mounted in each hub member, one for use as an ultrasonic transmitter and the other as an ultrasonic receiver, each transducer having its principal transmitting/receiving axis extending generally radially of the hub members in substantially the same plane containing the aligned axes of the hub members; and roller means rotatably mounted on said hub members, said roller means being adapted to make rolling contact with said object and to conduct ultrasonic signals from said one transducer to the object and from the object to said other transducer.

Thus the spacing between the two transducers can be made relatively very small, in fact not much greater than the thickness of the acoustic screening member.

In a preferred embodiment of the invention, the respective transmitting/receiving axes of the transducers converge: preferably, said axes are both inclined towards a reference plane which perpendicularly bisects the line joining the transducers. In a particularly advantageous arrangement, the axis of the transducer serving as the transmitter is inclined at an angle of about 5° to this reference plane, while the axis of the transducer serving as the receiver is inclined at an angle of about 7° to this reference plane.

The roller means may conveniently comprise first and second substantially cylindrical cup-shaped members, preferably of a plastics material such as perspex or that available under the trade name VESPEL, each of which is coaxially and rotatably supported on a respective one of the hub members so as to define therearound a sealed chamber, the sealed chambers being filled with an acoustic coupling fluid such as glycerine. In this case, the acoustic screening member may conveniently comprise a disc of a suitable screening material, for example a cork-like material such as that available under the trade mark NEBAR, disposed between the adjacent bases of the cup-shaped members and bonded to one of the bases.

The roller means may further comprise a common tire which fits coaxially over both cup-shaped members, although the cup-shaped members may be provided with individual tires if desired.

The invention will now be described, by way of non-limitative example only, with reference to the accompanying drawing, which is an extremely diagrammatic sectional view of a roller-type ultrasonic inspection device in accordance with the present invention.

The roller-type ultrasonic device shown in the drawing is designated generally by reference 10, and comprises a supporting structure 12 having two approximately parallel limbs 14 between which the roller 16 of the device is rotatably supported as will hereinafter become apparent. The purpose of the supporting structure 12 is to permit the roller 16 to be brought into rolling contact with a workpiece or like object which is to be ultrasonically inspected.

Projecting from each of the limbs 14, towards the other limb, is a respective non-rotating, aluminum, stepped diameter stub axle or shaft 18. The shafts 18 are substantially identical, and each of them comprises a reduced diameter portion 20 secured to the adjacent limb 14, and an increased-diameter portion 22 which constitutes a hub. The two hubs 22 are thus adjacent each other, and define a gap 24 between them.

Each of the hubs 22 has a respective flat 26 machined on it, the flats being in corresponding angular positions on each hub and having respective cylindrical recesses 28 machined in them. The recesses 28 each extend radially into their respective hub 22, and communicate with respective passages 30 extending along the hub axis: the passages 30 communicate in turn with respective passages 34 in the limbs 14 of the supporting structure 12.

Each of the recesses 28 is closed by a respective plug 36 of aluminum or araldite, whose radially outer head 38 covers the flat 26 and is machined to conform to the remainder of the outer circumference of the hub 22. The radially inner end 40 of each plug 36 is flat, with its normal lying in the same plane as that for the other plug and inclined at a predetermined angle towards a plane perpendicular to the axis of the shafts 18 and passing between their adjacent hubs 22. A respective flat ultrasonic transducer 42, in the form of a thin, flat, approximately circular piezoelectric crystal (typically lead zirconate titanate), is bonded on the surface of the inner end 40 of each plug 36, and electrical leads 44 for conveying electrical signals to and from the transducers 42 extend through the passages 30, 34 to electronic energising and signal processing circuitry (not shown) of known kind, for example of the kind forming the basis of our UFD-S ultrasonic flaw detector instrument.

The roller 16 comprises two identical cylindrical cups 46 of a suitable plastics material, such as perspex or that available under the trade name VESPEL, these cups each being coaxially disposed around a respective one of the stub shafts 18 with their respective bases 48 adjacent and parallel to each other in the gap 24 between the hubs 22. Each cup 46 extends across the whole axial extent of the hub 22 of its respective shaft 18, and the rim of its open end is bonded in an annular groove 50 in a respective combined bearing and seal plate 52. Each plate 52 is rotatably supported on the reduced diameter portion 20 of its respective shaft 18 by a bearing 54, and is also sealed with respect to the portion 20 by means of a seal 56. Each cup 46 and its associated plate 52 therefore defines a sealed chamber 58 around its respective hub 22, and this chamber is filled with a combined acoustic coupling and lubricating fluid such as glycerine.

An acoustic screen 60, in the form of a disc of the cork-like material known as NEBAR, is positioned in the gap 24 by bonding it to the outside of the base 48 of one of the cups 46.

Finally, a single tire 62 of a suitable resilient material, such as RTV 668 A & B silicone compound available from ICI Ltd, coaxially surrounds and is a tight fit on both cups 46, the tyre being axially located on the cups by the plates 52.

In operation, the device 10 is urged into rolling contact with a moving sheet-like object, such as a sheet of carbon-fibre reinforced plastic (CFRP) or glass-fibre reinforced plastic (GFRP), to be ultrasonically investigated, the purpose of the investigation typically being to detect flaws such as small areas of inadequate or unsatisfactory bonding between the plastic and its reinforcing fibres.

One of the transducers 42 is connected to the aforementioned UFD-S instrument to be operated as an ultrasonic transmitter, while the other is connected to the instrument as an ultrasonic receiver. Since the radially inner portion of each recess 28 is air-filled, the transducers 42 are undamped and therefore operate in a broad-band mode (ie emitting or responding to a wide range of frequencies). Ultrasonic signals therefore pass downwardly (as viewed in the drawing) through the plug 36 associated with the transmitter transducer 42, through the glycerine, the respective cup 46 and the tire 62, and into the object. After reflection from the back (or far) wall of the object, the ultrasonic signals pass to the receiver transducer 42 via the tire 62, the respective cup 46, the glycerine and the respective plug 36. The presence of the aforementioned flaws affects the character of the ultrasonic signals passing to the receiver transducer 42 in a known and detectable manner, thus permitting the presence of such flaws to be reliably detected.

The principal transmitting/receiving axes of the transducers 42 are perpendicular to the plane of the crystals constituting them, and are thus aligned with respective ones of the aforementioned normals to the flat inner ends 40 of the plugs 36. The aforementioned predetermined angles of inclination of these normals (much exaggerated in the drawing) are 5° for the transmitter and 7° for the receiver. This has been found by experiment to give particularly good results for the device 10, for which the roller 16 is about 4.8 cm wide and about 2 cm in diameter.

It will be appreciated that the two transducers 42 are extremely close together, thus permitting detailed ultrasonic investigation of a particularly narrow strip of the object under test and the detection of very small flaws. However, direct ultrasonic transmissions from the transducer 42 serving as the transmitter to the one serving as the receiver are minimised by the acoustic screen 60.

Several modifications can be made to the ultrasonic device 10. For example, suitable materials other than those specifically mentioned can be used, e.g. stainless steel instead of aluminum for the shafts 18. Additionally the tire 62 can if desired be replaced by two axially adjacent tires, one for each cup 46.

Another important modification which can be made to the device 10 is to replace the individual cups 46 by a single cylindrical sleeve which extends coaxially between the combined bearing and seal plates 52, thus defining a single sealed chamber around both hubs 22. In this case, the acoustic screen 60 is simply bonded between the two adjacent hubs 22. It will be appreciated that the axial extent of the gap 24 in this embodiment can be substantially less than in the illustrated embodiment having the two cups 46.

Finally, the device 10 has applications other than that specifically mentioned. For example, it can be used in the ultrasonic investigation of many different composite and/or laminated materials, particularly for detecting and locating bonding defects. Also, it can be used to effect continuous thickness measurements on many different materials, including metals.

I claim:

1. A roller-type ultrasonic inspection device for use in the ultrasonic inspection of an object, the device comprising:

a support having two spaced-apart generally parallel limbs;

two substantially coaxially aligned hub members each projecting from a respective one of the limbs towards the other hub member, the adjacent ends of the hub members defining a gap therebetween;

an acoustic isolation member disposed in said gap;

a respective ultrasonic transducer mounted in each hub member, one for use as an ultrasonic transmitter and the other as an ultrasonic receiver, each transducer being arrangd such that its principal transmitting/receiving axis extends generally radially of the hub members, both axes being in substantially the same plane, and such that said plane also contains the axis of alignment of the hub members; and roller means rotatably mounted on said hub members, said roller means being adapted to make rolling contact with said object and to conduct ultrasonic signals from said one transducer to the object and from the object to said other transducer, wherein coupling between each transducer and said roller means is by means of a fluid surrounding each hub and the fluid associated with each hub is acoustically separated by said acoustic isolation member.

2. A roller-type ultrasonic inspection device as claimed in claim 1, wherein the respective transmitting/receiving axes of the transducers converge.

3. A roller-type ultrasonic inspection device as claimed in claim 2, wherein the respective transmitting/receiving axes of the transducers are both inclined towards a reference plane which perpendicularly bisects the line joining the transducers.

4. A roller-type ultrasonic inspection device as claimed in claim 3, wherein the axis of the transducer serving as the transmitter is inclined at an angle of about 5° to said reference plane, while the axis of the transducer serving as the receiver is inclined at an angle of about 7° to said reference plane.

5. A roller-type ultrasonic inspection device as claimed in claim 1, wherein the roller means comprises first and second substantially cylindrical cup-shaped members, each of which is coaxially and rotatably supported on a respective one of the hub members so as to define therearound a sealed chamber, the sealed chambers being filled with an acoustic coupling fluid such as glycerine.

6. A roller-type ultrasonic inspection device as claimed in claim 5, wherein the acoustic isolation member comprises a disc of a suitable isolation material disposed between the adjacent bases of the cup-shaped members.

7. A roller-type ultrasonic inspection device as claimed in claim 6, wherein the acoustic isolation member is bonded to at least one of said bases and substantially fills the space between said bases.

8. A roller-type ultrasonic inspection device as claimed in claim 6, wherein the acoustic isolation member comprises a disc of a cork-like material.

9. A roller-type ultrasonic inspection device as claimed in claim 5, wherein the roller means further comprises a common tire which fits coaxially over both cup-shaped members.

* * * * *